United States Patent [19]
Goddard et al.

[11] Patent Number: 5,411,848
[45] Date of Patent: May 2, 1995

[54] PHOTOGRAPHIC COLOR COUPLERS AND PHOTOGRAPHIC MATERIALS CONTAINING THEM

[75] Inventors: John D. Goddard, Pinner; Danuta Gibson, Garston, both of United Kingdom

[73] Assignee: Eastman Kodak Company, Rochester, N.Y.

[21] Appl. No.: 275,218

[22] Filed: Jul. 14, 1994

[30] Foreign Application Priority Data

Aug. 16, 1993 [GB] United Kingdom ............... 9317035

[51] Int. Cl.$^6$ ............................................. G03C 7/36
[52] U.S. Cl. ................................... 430/557; 430/387
[58] Field of Search ............... 430/556, 557, 386, 387

[56] References Cited

U.S. PATENT DOCUMENTS

| | | | |
|---|---|---|---|
| 3,674,490 | 7/1972 | Matejec | 96/48 |
| 3,675,891 | 10/1973 | Travis | 96/55 |
| 4,567,135 | 1/1986 | Arakawa et al. | 430/557 |
| 4,705,743 | 11/1987 | Mihayashi et al. | 430/557 |
| 5,340,703 | 8/1994 | Masumi et al. | 430/557 |

FOREIGN PATENT DOCUMENTS 1403418 8/1975 United Kingdom .
1560572 2/1980 United Kingdom .

*Primary Examiner*—Lee C. Wright
*Attorney, Agent, or Firm*—Arthur E. Kluegel

[57] ABSTRACT

A photographic element, and coupler employed therein, comprises a photographic silver halide emulsion layer containing a yellow dye-forming coupler having a the general formula:

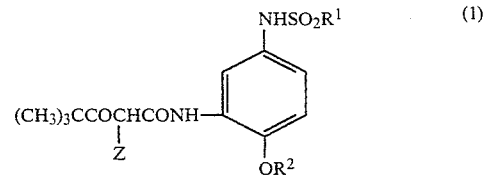

wherein Z is a ballasted group which splits off on silver halide development which is of such size and configuration to render the coupler non-diffusible in photographic layers, prior to splitting off, and $R^1$ and $R^2$ are each individually an alkyl or aryl group whose combined effect is to render the yellow dye formed on coupling sufficiently mobile to produce image smearing.

6 Claims, 1 Drawing Sheet

PHOTOGRAPHIC COLOR COUPLERS AND PHOTOGRAPHIC MATERIALS CONTAINING THEM

FIELD OF THE INVENTION

This invention relates to photographic colour couplers and photographic materials containing them and particularly to yellow dye-forming couplers.

BACKGROUND OF THE INVENTION

Redox amplification processes have been described, for example in British Specification Nos. 1,268,126, 1,399,481, 1,403,418 and 1,560,572. In such processes colour materials are developed to produce a silver image (which may contain only small amounts of silver) and then treated with a redox amplifying solution (or a combined developer-amplifier) to form a dye image. The developer-amplifier solution contains a reducing agent, for example a colour developing agent, and an oxidising agent which will oxidise the colour developing agent in the presence of the silver image which acts as a catalyst. The photographic material used in such a process may be a conventional coupler-containing silver halide material or an image transfer material containing redox dye releasers. Oxidised colour developer reacts with a colour coupler (usually contained in the photographic material) to form image dye. The amount of dye formed depends on the time of treatment or the availability of colour coupler rather than the amount of silver in the image as is the case in conventional colour development processes. Examples of suitable oxidising agents include peroxy compounds including hydrogen peroxide and compounds which provide hydrogen peroxide, eg addition compounds of hydrogen peroxide; cobalt (III) complexes including cobalt hexammine complexes; and periodates. Mixtures of such compounds can also be used. A particular application of this technology is in the processing of silver chloride colour paper, especially such paper with low silver levels.

A problem encountered with such low silver materials designed to be processed by an redox amplification process is that the image dyes produced, especially in the yellow dye-forming layers, have a lower than expected covering power.

SUMMARY OF THE INVENTION

According to the present invention there are provided photographic yellow dye-forming couplers having the general formula:

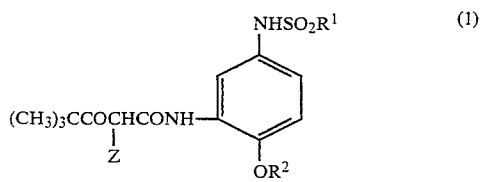

(1)

wherein Z is a ballasted group which splits off on silver halide development which is of such size and configuration to render the coupler non-diffusible in photographic layers, $R^1$ and $R^2$ are each individually an alkyl or aryl group whose combined effect is to render the yellow dye formed on coupling sufficiently mobile to produce image smearing.

The present invention also provides a photosensitive photographic silver halide material comprising a support bearing at least one silver halide emulsion layer having associated therewith a yellow dye-forming coupler of the general formula (1) defined above.

The couplers of the present invention can produce dyes of desirable $\lambda_{max}$ in low silver photographic materials which have improved covering power.

DETAILED DESCRIPTION OF THE INVENTION

Figure 1:
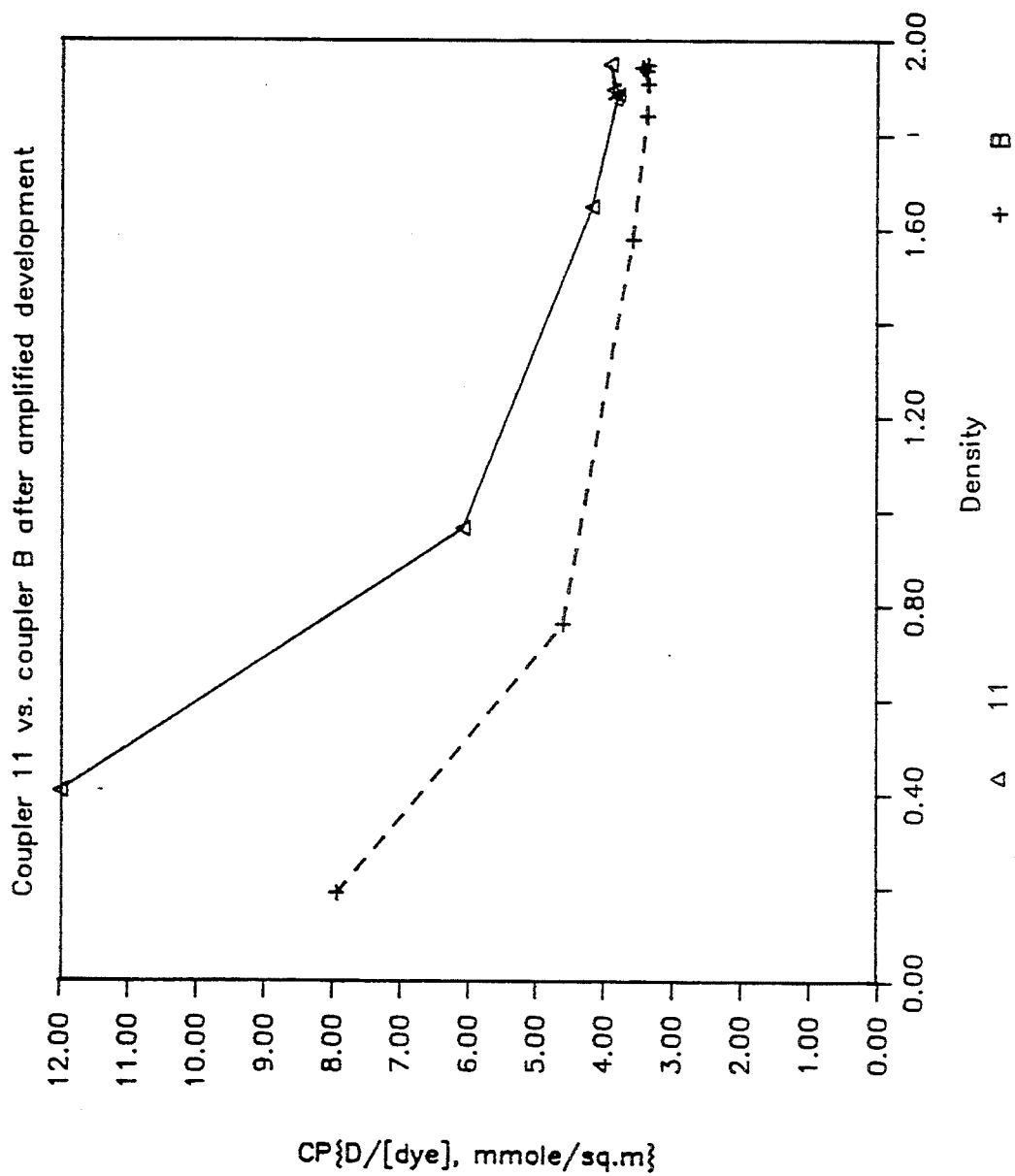
FIG. 1 is a graph showing the improved covering power of a photographic element employing a coupler in accordance with the invention vs. a comparison.

Examples of groups which split off on coupling include halogen, carboxy, heterocyclyl joined via a ring carbon or hetero atom in the heterocyclic nucleus, —OR⁴, —SR⁴, where R4 is an alkyl or aryl group either of which may be substituted, arylazo or heterocyclylazo. The group which splits off may provide a photographically useful compound. Many such groups are often known as photographically useful groups and they provide developer inhibitors, bleach accelerators, developer accelerators, antifoggants, competing couplers, etc. Many examples are listed in Research Disclosure Item 308119, December 1989 published by Kenneth Mason Publications, Emsworth, Hants, United Kingdom.

Preferred ballast groups are alkyl groups having 6 to 22 carbon atoms, alkylaryl or arylalkyl groups groups having a total of 18 to 26 carbon atoms both of which may be substituted and the carbon chains of the alkyl groups may be interrupted by heteroatoms.

In one embodiment the coupling-off group Z may have the formula:

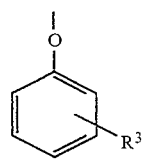

in which $R^3$ is a ballasting group of such size and configuration to render the coupler non-diffusible in photographic layers and the ring to which $R^3$ is attached may bear further substituents.

Examples of further coupling-off groups that Z may represent are:

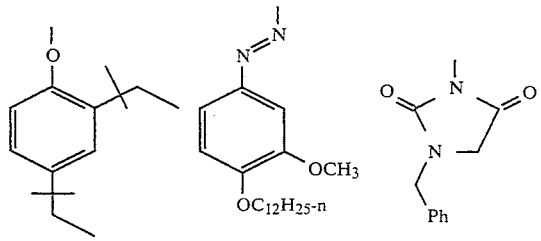

-continued

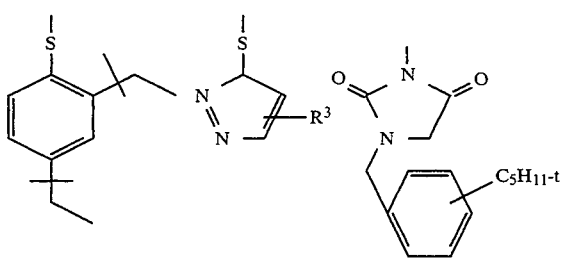

Specific examples of ballast groups that may be employed are those of the following formulae:

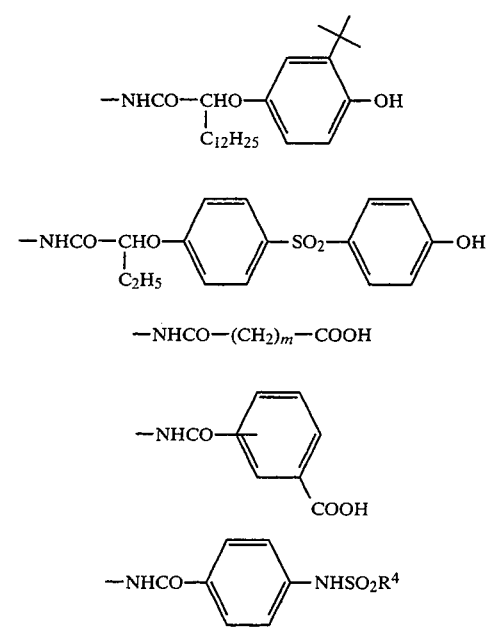

Two preferred groups of ballast group $R^3$ have one of the general formulae:

$-SO_2N(R^5)R^6-CH_3$     (2)

or $-COOR^6-CH_3$     (3)

wherein $R^5$ is hydrogen or an alkyl group of 1 or 2 carbon atoms, and $R^6$ is an alkyl group of 6 to 22 carbon atoms. Examples of groups which $R^1$ may represent are alkyl groups of 1 to 6 carbon atoms or phenyl. The preferred alkyl groups are methyl, ethyl, n-butyl, n-pentyl and n-hexyl.

Examples of groups which $R^2$ may represent are methyl, ethyl, propyl or n-butyl.

Examples of groups which $R^5$ may represent are straight or branched chain alkyl groups of 6 to 22 carbon groups, for example n-hexadecyl, iso-octyl, or—$CH_2CH(C_2H_5)$-$(CH_2)_3$—$CH_3$.

Specific couplers according to the present invention are listed in Tables 1, 2 and 3 below.

TABLE 1

(4)

$(CH_3)_3CCOCHCONH$— with $NHSO_2R^1$, $OR^2$, and $SO_2NR^5(CH_2)_{17}CH_3$ substituents

| Coupler No. | $R^1$ | $R^2$ | $R^5$ |
|---|---|---|---|
| 1 | —$(CH_2)_5CH_3$ | $CH_3$ | $CH_3$ |
| 2 | —$(CH_2)_2CH_3$ | $CH_3$ | $CH_3$ |
| 3 | 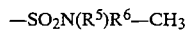 | $CH_3$ | $CH_3$ |
| 4 | —$CH_3$ | $CH_3$ | $CH_3$ |
| 5 | —$(CH_2)_3CH_3$ | $CH_3$ | $CH_3$ |
| 6 | —$CH_3$ | $CH_3$ | H |

TABLE 2

(5)

$(CH_3)_3CCOCHCONH$— with $NHSO_2R^1$, $OR^2$, and $COOR^7$ substituents

| Coupler No. | $R^1$ | $R^2$ | $R^7$ |
|---|---|---|---|
| 7 | $CH_3$ | $CH_3$ | —$CH_2CH(C_2H_5)$—$(CH_2)_3CH_3$ |
| 8 | $CH_3$ | $CH_3$ | —$(CH_2)_{15}CH_3$ |
| 9 |  | $CH_3$ | —$(CH_2)_{15}CH_3$ |

TABLE 3

$(CH_3)_3CCOCHCONH$— with $NHSO_2Me$, $OMe$, $R^8$, $R^9$ substituents

| Coupler No. | $R^8$ | $R^9$ |
|---|---|---|
| 10 | H | —$SO_2NHCH_2CH_2OOC(CH_2)_{16}Me$ |
| 11 | —$NHSO_2(CH_2)_{15}Me$ | —COOMe |
| 12 | —$NHSO_2Me$ | —$COO(CH_2)_{15}Me$ |

TABLE 3-continued

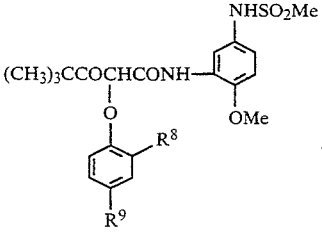

| Coupler No. | R[8] | R[9] |
|---|---|---|
| 13 | H | 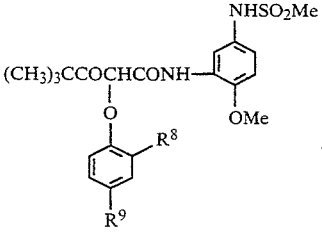 |

The couplers of formula (1) may be made by methods in themselves known. For example the following route may be followed:

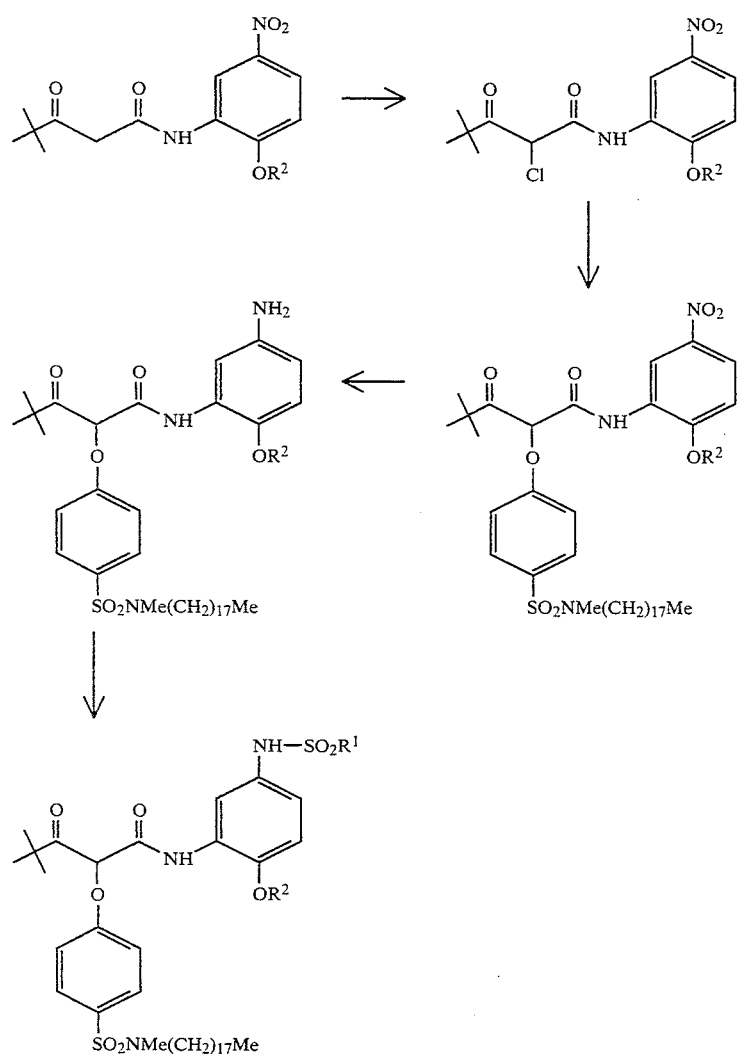

The dye-forming couplers of this invention can be used in the ways and for the purposes that dye-forming couplers have been previously used in the photographic art.

Typically, the couplers are associated with a silver halide emulsion layer coated on a support to form a photographic element. As used herein, the term "associated with" signifies that the coupler is incorporated in the silver halide emulsion layer or in a layer adjacent thereto where, during processing, it is capable of reacting with silver halide development products.

In a preferred embodiment the photographic material comprises a resin-coated paper support and the emulsion layers comprise more than 80%, preferably more than 90% silver chloride and are more preferably composed of substantially pure silver chloride. The photographic elements can be single colour elements or multicolour elements.

In a multicolour element, the magenta dye-forming couplers of this invention would usually be associated with a green-sensitive emulsion, although they could be associated with an emulsion sensitised to a different region of the spectrum, or with a panchromatically sensitised, orthochromatically sensitised or unsensitised emulsion. Multicolour elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

The photographic materials can be single colour materials or multicolour materials. Multicolour materials contain dye image-forming units sensitive to each of the three primary regions of the spectrum. Each unit can be comprised of a single emulsion layer or of multiple emulsion layers sensitive to a given region of the spectrum. The layers of the materials, including the layers of the image-forming units, can be arranged in various orders as known in the art.

A typical multicolour photographic element comprises a support bearing yellow, magenta and cyan dye image-forming units comprising at least one blue-, green- or red-sensitive silver halide emulsion layer having associated therewith at least one yellow, magenta or cyan dye-forming coupler respectively, at least one of the magenta dye-forming couplers being a coupler of this invention. The element can contain additional layers, such as filter and barrier layers. In the following discussion of suitable materials for use in the emulsions and elements of this invention, reference will be made to Research Disclosure Item 308119, December 1989 published by Kenneth Mason Publications, Emsworth, Hants, United Kingdom. This publication will be identified hereafter as "Research Disclosure".

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

The elements of the invention can include additional couplers as described in Research Disclosure Section VII, paragraphs F G and H and the publications cited therein. The couplers of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilisers (see Research Disclosure Section VI), antistain agents and image dye stabiliser (see Research Disclosure Section VII, paragraphs I and J), light absorbing and scattering materials (see Research Disclosure Section VIII), hardeners (see Research Disclosure Section X), plasticisers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Preferred colour developing agents are p-phenylene diamines. Especially preferred are 4-amino-3-methyl-N,N-diethylaniline hydrochloride, 4-amino-3-methyl-N-ethyl-N-b-(methanesulphonamido)- ethylaniline sulphate hydrate, 4-amino-3-methyl-N- ethyl-N-b-hydroxyethylaniline sulphate, 4-amino-3-b-(methanesulphonamido)ethyl-N,N-diethylaniline hydrochloride and 4-amino-N-ethyl-N-(2-methoxyethyl)-m-toluidine di-p-toluene sulphonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

The colour photographic material may be of any type but will preferably contain low amounts of silver halide. Preferred silver halide coverages are in the range 0.1 to 20, preferably 0.1 to 3 mg/m$^2$ (as silver).

The processing preferably comprises a redox image amplification step referred to above. Such a process can comprise a colour development step followed by an amplification step or developer/amplification step, or a single developer/amplification step.

The dye-forming couplers of this invention can be used in the ways and for the purposes that dye-forming couplers have been previously used in the photographic art.

Typically, the couplers are associated with a silver halide emulsion layer coated on a support to form a photographic element. As used herein, the term "associated with" signifies that the coupler is incorporated in the silver halide emulsion layer or in a layer adjacent thereto where, during processing, it is capable of reacting with silver halide development products.

The photographic elements can be single colour elements or multicolour elements. In a multicolour element, the magenta dye-forming couplers of this invention would usually be associated with a green-sensitive emulsion, although they could be associated with an emulsion sensitised to a different region of the spectrum, or with a panchromatically sensitised, orthochromatically sensitised or unsensitised emulsion. Multicolour elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolour photographic element comprises a support bearing yellow, magenta and cyan dye image-forming units comprising at least one blue-, green- or red-sensitive silver halide emulsion layer having associated therewith at least one yellow, magenta or cyan dye-forming coupler respectively, at least one of the yellow dye-forming couplers being a coupler of this invention. The element can contain additional layers, such as filter and barrier layers.

In the following discussion of suitable materials for use in the emulsions and elements of this invention, reference will be made to Research Disclosure Item 308119, December 1989 published by Kenneth Mason Publications, Emsworth, Hants, United Kingdom. This publication will be identified hereafter as "Research Disclosure".

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

The elements of the invention can include additional couplers as described in Research Disclosure Section VII, paragraphs F G and H and the publications cited therein. The couplers of this invention and any additional couplers can be incorporated in the elements and emulsions as described in Research Disclosures of Section VII, paragraph C and the publications cited therein.

The photographic elements of this invention or individual layers thereof, can contain brighteners (see Research Disclosure Section V), antifoggants and stabilisers (see Research Disclosure Section VI), antistain agents and image dye stabiliser (see Research Disclosure Section VII, paragraphs I and J), light absorbing and scattering materials (see Research Disclosure Section VIII), hardeners (see Research Disclosure Section X), plasticisers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein. Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a colour developing agent to reduce developable silver halide and oxidise the colour developing agent. Oxidised colour developing agent in turn reacts with the coupler to yield a dye.

Preferred colour developing agents are p-phenylene diamines. Especially preferred are 4-amino-3-methyl-N,N-diethylaniline hydrochloride, 4-amino-3-methyl-N-ethyl-N-b-(methanesulphonamido)- ethylaniline sulphate hydrate, 4-amino-3-methyl-N- ethyl-N-b-hydroxyethylaniline sulphate, 4-amino-3-b-(methanesulphonamido)ethyl-N,N-diethylaniline hydrochloride and 4-amino-N-ethyl-N-(2-methoxyethyl)-m-toluidine di-p-toluene sulphonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following Examples are included for a better understanding of the invention.

EXAMPLE 1

The couplers indicated below were incorporated into dispersions using dibutyl phthalate as main solvent and 2-(2-butoxyethoxy)ethyl acetate as auxiliary solvent at a ratio of 1:0.5:0.25 coupler:main solvent:auxiliary solvent. The dispersions were coated in the yellow imaging layer at a coupler laydown of 0.70 mmoles/m$^2$. Coatings of the following structure were prepared:

| | |
|---|---|
| Gelatin | 1.61 g/m$^2$ |
| Silver chloride emulsion (as Ag) | 48.4 mg/m$^2$ |
| Coupler | 0.70 mmole/m$^2$ |
| Gelatin | 1.61 g/m$^2$ |
| Gelatin | 1.08 g/m$^2$ |
| /// Resin coated paper support /// | |

Strips of the single colour coating were exposed to a step wedge for 0.1 sec and processed for secs at 32° C. in a developer/amplifier of the formulation:

| | |
|---|---|
| Potassium carbonate | 10.0 g |
| 60% 1-hydroxyethylidene-1,1'-diphosphonic acid | 0.6 g |
| 41% Diethyltriamine-pentaacetic acid | 2.0 ml |
| Potassium bromide | 1.0 mg |
| Potassium chloride | 0.35 g |
| Diethylhydroxylamine (85%) | 4.0 ml |
| 4-N-ethyl-N-(b-methanesulphonamidoethyl)-o-toluidine sesquisulphate (CD3) | 3.5 g |
| Hydrogen peroxide (30%) | 5.0 g |
| Water to | 1.0 l |
| pH adjusted to 10.3 with sodium hydroxide | |

This was followed by 30 secs in a 15 g/l solution of sodium metabisulphite and 37 secs in a fix solution of the formulation:

| | |
|---|---|
| Ammonium thiosulphate | 120.0 g |
| Sodium sulphite (anhy) | 20.0 g |
| Potassium metabisulphite | 20.0 g |
| Water to 1.0 liter | | then washed and dried.

Normalised dye hue curves of the present couplers and comparative prior art couplers were obtained (in reflection mode) and other sensitometric data were obtained for each strip of the exposed and processed coatings. Control coatings using and/or of higher silver laydown but otherwise similar characteristics were processed in a standard RA4 process. The results are tabulated below.

TABLE 3

| Coupler Number | Coupler laydown (mmol/m$^2$) | Sliver laydown (mg/m$^2$) | $\lambda_{max\ (nm)}$ | Blue $D_{min}$ | Blue $D_{max}$ | Contrast |
|---|---|---|---|---|---|---|
| B | 1.190 | 270.1 | 452 | 0.087 | 2.09 | 2.76 |
| B | 1.190 | 48.4 | 452 | 0.071 | 2.02 | 2.66 |
| A | 0.7 | 48.4 | 462 | 0.071 | 2.15 | 2.50 |
| 4 | 0.7 | 48.4 | 445 | 0.092 | 2.23 | 2.87 |
| 5 | 0.7 | 48.4 | 444 | 0.081 | 1.76 | 2.51 |
| 5 | 0.7 | 48.4 | 442 | 0.097 | 2.20 | 2.86 |
| B | 1.190 | 270.1 | 452 | 0.072 | 2.10 | 2.64 |
| A | 0.7 | 48.4 | 461 | 0.104 | 2.25 | 3.10 |
| 1 | 0.7 | 48.4 | 445 | 0.069 | 2.14 | 3.41 |
| 2 | 0.7 | 48.4 | 445 | 0.076 | 1.31 | 2.07 |

TABLE 3-continued

| Coupler Number | Coupler laydown (mmol/m²) | Silver laydown (mg/m²) | $\lambda_{max}$ (nm) | Blue $D_{min}$ | Blue $D_{max}$ | Contrast |
|---|---|---|---|---|---|---|
| 9 | 0.7 | 48.4 | 445 | 0.061 | 1.92 | 2.65 |
| B | 1.19 | 270.1 | 453 | 0.147 | 2.17 | 2.95 |
| B | 1.19 | 48.4 | 453 | 0.083 | 1.97 | 2.51 |
| A | 0.7 | 48.4 | 462 | 0.158 | 2.10 | 3.07 |
| 12 | 0.7 | 48.4 | 447 | 0.122 | 1.83 | 2.75 |
| 11 | 0.7 | 48.4 | 445 | 0.105 | 2.06 | 2.93 |
| 13 | 0.7 | 48.4 | 447 | 0.092 | 2.05 | 3.21 |

The comparison couplers had the following formulae:

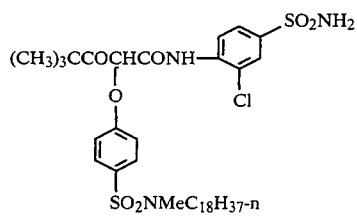
(A)

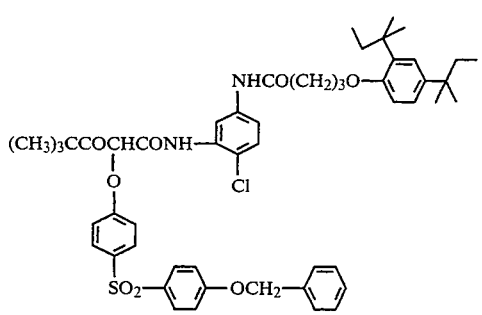
(B)

Dye (A) has a similar structure to those of the invention but has an undesirable hue while Dye (B) has a more desirable hue but does not smear.

The data show that all the couplers of the invention provide dye hues which are hypsochromic to the dye produced by Comparative Coupler (B) which is used commercially and even more hypsochromic to the dye produced by Comparative Coupler (A). Cross sections of the exposed and processed coatings show that for some of the couplers, diffusion of dye into the mordant layer had occurred; Dmin was lower for many of the couplers and contrast higher. For other couplers, smearing of the dyes is restricted to the dye clouds. However, if the coated strips of the latter are processed through developer of higher pH (up to 12) or if the coated strips are passed through a pH11 or pH12 bath prior to washing, the dye clouds become larger and more diffuse as the pH of the process is increased.

Analysis of the dye and coupler laydowns in exposed and processed coatings of coupler 11 and comparative coupler B showed that coupler 11 provided greater dye covering power (See FIG. 1 of the accompanying drawings).

We claim:

1. A photographic element comprising a photographic silver halide emulsion layer containing yellow dye-forming coupler having a the general formula:

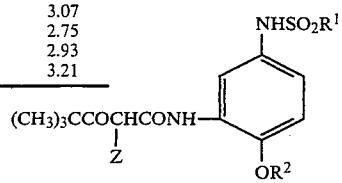
(1)

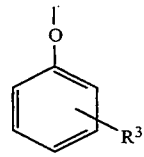
(1)

wherein Z is a ballasted group which splits off on silver halide development which is of such size and configuration to render the coupler non-diffusible in photographic layers, prior to splitting off, and $R^1$ and $R^2$ are each individually an alkyl or aryl group whose combined effect is to render the yellow dye formed on coupling sufficiently mobile to produce image smearing.

2. An element as claimed in claim 1 in which the coupling-off group Z has the formula:

in which $R^3$ is a ballasting group of such size and configuration to render the coupler non-diffusible in photographic layers and in which the ring to which $R^3$ is attached may bear further substituents.

3. An element as claimed in claim 2 in which ballast group $R^3$ is an alkyl group having 6 to 22 carbon atoms, or an alkylaryl or arylalkyl group having a total of 18 to 26 carbon atoms, both of which may be substituted, and the carbon chains of the alkyl groups may be interrupted by heteroatoms.

4. An element as claimed in claim 2 in which $R^3$ has one of the general formulae:

$$-SO_2N(R^5)R^6-CH_3 \qquad (2)$$

or $$-COOR^6-CH_3 \qquad (3)$$

wherein $R^5$ is hydrogen or an alkyl group of 1 or 2 carbon atoms, and $R^6$ is an divalent saturated aliphatic group of 6 to 22 carbon atoms.

5. An element as claimed in claim 1 in which $R^1$ is an alkyl group of 1 to 6 carbon atoms or phenyl.

6. An element as claimed in claim 1 in which $R^2$ is methyl, ethyl, propyl or n-butyl.

* * * * *